(12) United States Patent
Arofikin

(10) Patent No.: US 7,708,941 B2
(45) Date of Patent: May 4, 2010

(54) LIQUID PRODUCT PRESSURE TREATMENT METHOD AND DEVICE

(75) Inventor: Nikolay Vladislavovich Arofikin, Moscow (RU)

(73) Assignee: Millisecond Technologies Corp., New York, NY (US)

( * ) Notice: Subject to any disclaimer, the term of this patent is extended or adjusted under 35 U.S.C. 154(b) by 0 days.

(21) Appl. No.: 11/821,216

(22) Filed: Jun. 22, 2007

(65) Prior Publication Data

US 2008/0038150 A1    Feb. 14, 2008

Related U.S. Application Data

(63) Continuation-in-part of application No. PCT/IB2005/003879, filed on Dec. 22, 2005.

(51) Int. Cl.
*A61L 2/02*    (2006.01)

(52) U.S. Cl. ............. 422/39; 426/476; 99/453; 99/483

(58) Field of Classification Search ............ 422/39; 426/476; 99/453; 210/600
See application file for complete search history.

(56) References Cited

U.S. PATENT DOCUMENTS

| | | | | |
|---|---|---|---|---|
| 1,711,097 | A * | 4/1929 | Kratzer | 422/39 |
| 1,819,023 | A * | 8/1931 | Grindrod | 426/476 |
| 2,374,805 | A * | 5/1945 | Camelford | 422/39 |
| 5,232,726 | A | 8/1993 | Clark et al. | |
| 6,471,914 | B2 | 10/2002 | Platz et al. | |
| 6,749,809 | B2 * | 6/2004 | Karasawa | 422/39 |
| 2002/0020675 | A1 * | 2/2002 | Herrington et al. | 210/748 |
| 2004/0161363 | A1 * | 8/2004 | Lutzer | 422/38 |

FOREIGN PATENT DOCUMENTS

| | | | |
|---|---|---|---|
| FR | 2735039 | A | 12/1996 |
| FR | 2735039 | A * | 12/1996 |
| JP | 401097459 | A * | 4/1989 |
| JP | 2001346515 | A | 12/2001 |
| WO | 9732483 | A | 9/1997 |

* cited by examiner

*Primary Examiner*—Elizabeth L McKane
(74) *Attorney, Agent, or Firm*—David E. Rogers; Lucius L. Lockwood; Squire, Sanders & Dempsey L.L.P.

(57) ABSTRACT

A method and device related to a liquid product pressure and (optionally) temperature treatment method reduces the level of microorganisms in the liquid product to a preselected level. Utilizing the method, liquid product is diffused in a chamber with the speed of pressure variation of liquid product in one embodiment of about $10^9$ Pa/sec. The preferred speed of the diffused drops is about 10 m/sec. The liquid product can optionally be heated before or during diffusion, and is preferably heated as a diffused liquid product by mixing it with superheated steam. The device includes a chamber and a diffuser in communication with the chamber. Optionally, the device may include a heating apparatus, such as a steam generator connected via a pressure control valve to a steam super heater, a cooling chamber connected via a pressure control valve with a condenser, a vacuum pump in communication with the chamber, units for condensation and collecting finished products and a vacuum control unit in communication with the chamber.

9 Claims, 1 Drawing Sheet

LIQUID PRODUCT PRESSURE TREATMENT METHOD AND DEVICE

RELATED APPLICATION

Figure 1:
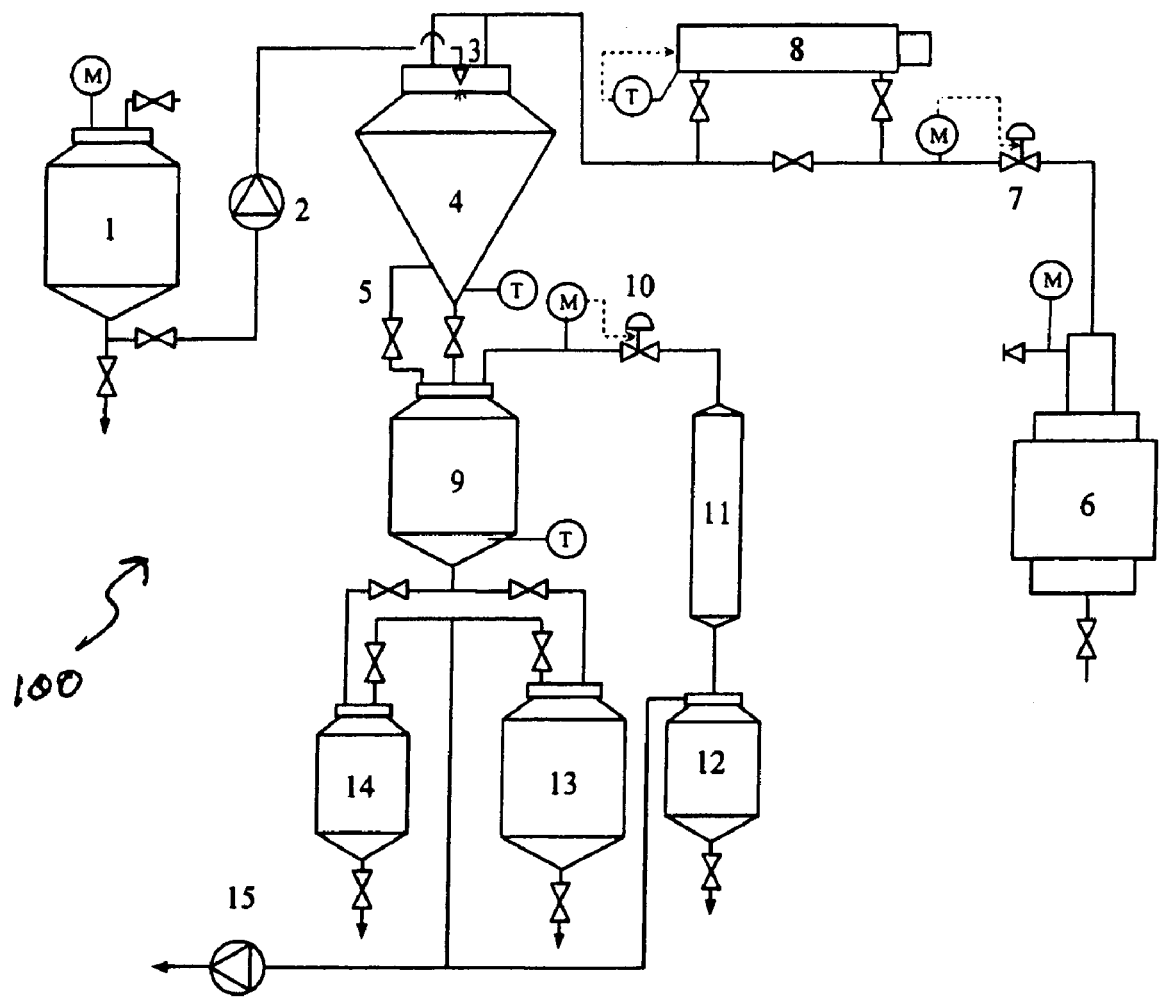

This application is a continuation-in-part of and claims priority to International Application No. PCT/IB2005/003879, filed Dec. 22, 2005, which claims priority to Russian Federation Application Serial No. 2004137687/13(040980), filed Dec. 23, 2004 by inventors Andrie A. Volkov, Nikolay V. Arofikin and Alexander Y. Kolesnov, the disclosures of which are incorporated herein in their entirety for all purposes.

FIELD OF THE INVENTION

The invention is intended for use in any product in which it is necessary to reduce the numbers of microorganisms, and is related to a liquid product pressure and (optionally) temperature treatment method that kills microorganisms, such as bacteria. The method can be used for liquid products or substances in any industry, such as the food or pharmacological industries.

BACKGROUND

There is a known method of liquid product thermal treatment intended to destroy harmful microorganisms (also referred to herein as microorganisms) wherein microorganisms are killed by mixing liquid product with a heating medium (e.g., sterile water steam) thereby heating the liquid product, and maintaining it at a temperature that ensures pasteurization or sterilization.

One drawback of this known method is that the liquid product mixes with water when steam condenses during the process of product cooling. This increases product mass on average by about 30% and as a result water removal is necessary. The water removal is connected with additional steps and expenses. Another drawback of this known method is potential deterioration of product quality and taste after pasteurization due to destruction of vitamins and protein coagulation because of the temperature to which the product is raised.

Another known method with similar technical characteristics is one in which liquid product is mixed with a heating medium of condensing steam, and the liquid product is heated at a rate of about 1400° C./sec or more for pasteurization and about 7600° C./sec or more for sterilization to a temperature not exceeding the temperature at which qualitative changes in liquid product takes place (such qualitative changes and temperatures being known to those skilled in the art). The product is diffused into drops preferably not exceeding 0.3 mm in diameter (this process is described in Russian Patent No. 2,052,967, the disclosure of which that is not inconsistent with the disclosure herein, is incorporated by reference). This method promotes efficient thermal treatment of the liquid product, sufficiently kills microorganisms and does not adversely impact the qualitative aspects of the liquid product, because it increases the rate at which the liquid product is heated and only maintains the product at a high temperature for a short duration. The liquid product is heated only to a temperature lower than that which does not effect qualitative changes in the liquid product. This method is performed in a pasteurization device, which contains a liquid product diffuser, a pasteurization chamber, a nozzle for steam, a steam generator, a cooling chamber, and a vacuum pump.

A drawback of this method is that it does not exclude mixing of product with steam condensate, and this can adversely impact the organoleptic and physicochemical (such as taste, odor, color and consistency) stability of such liquid products, which include as non-frozen concentrate ("NFC") juices, and it does not guarantee the necessary destruction of microorganisms that are heat resistant.

SUMMARY OF THE INVENTION

The purpose of the invention is to create an efficient liquid product pressure and (optionally) temperature treatment method and device that promote organoleptic and physicochemical stability of liquid products. It has been discovered that exposing a liquid product to a sharp pressure differential, which may or may not be associated with heating the liquid product, destroys microorganisms, including microorganisms that are heat resistant.

The problem can be solved by diffusing liquid product into drops (preferably into drops not exceeding about 0.3 mm in diameter) and exposing the liquid product to a speed of pressure variation of about $10^9$ Pa/sec or more. Alternatively, the liquid product is exposed to a speed of pressure variation of at least about $10^5$ Pa/sec. In the preferred embodiment the speed of the drops speed is about 10 m/sec or more and the pressure variation occurs during diffusion of the liquid product. The liquid product is diffused utilizing a nozzle and is maintained at one pressure on one side of the nozzle (the pressure being measurable and controllable, preferably by using a pump) and is released when diffused into a chamber on the other side of the nozzle where it has a second pressure. The pressure of the chamber may also be regulated and if it is, it is preferably regulated by the use of a vacuum pump. The chamber is preferably maintained at a pressure at or lower than ambient pressure. In one embodiment, the chamber is maintained at a pressure lower than ambient pressure. In the preferred embodiment, a vacuum source is connected to the chamber and the pressure in the chamber is maintained at about 0.25 Pa.

Optionally, the liquid product can also be heated during the process. If so, the heating is preferably performed in the chamber as the liquid product is diffused and can be done utilizing superheated steam or any other suitable heating method (other options include ultrasonic frequency or infrared light). Other suitable heating methods include heating the walls of the chamber into which the liquid product is diffused. The liquid product can also be heated by heating the walls of the chamber into which the liquid product is diffused without direct contact with the walls of the chamber. If steam is used it is preferably introduced into the chamber through a separate nozzle and is delivered in the same direction as the liquid product. Further, the rate of heating the liquid product preferably does not exceed 1100° C./sec in the preferred embodiment, but any rate of heating can be utilized that sufficiently kills the required number of microorganisms and that does not heat the liquid product to a temperature at which its qualitative attributes are adversely affected. The heating step can be performed at a pressure at or lower than ambient temperature. In one embodiment, the heating step is performed at a pressure lower than ambient pressure.

A device for carrying out a method according to the invention preferably includes a chamber with a diffuser (preferably a nozzle), an optional heat source (preferably a steam generator, an opening for releasing steam (if steam is used) into the chamber, a cooling chamber, an optional vacuum pump connected to the chamber and a vacuum control valve, and an optional steam super heater.

The technical result of the invention is a highly efficient treatment method. The result is reached by the effect of short time product pressure change, which may be coupled with short time heating. The process yields a required level (determined based upon the applicable governmental standard) of microbiological stability for liquid products without significant changes in their organoleptic or physicochemical features.

DETAILED DESCRIPTION OF PREFERRED EMBODIMENTS

Figure 2:
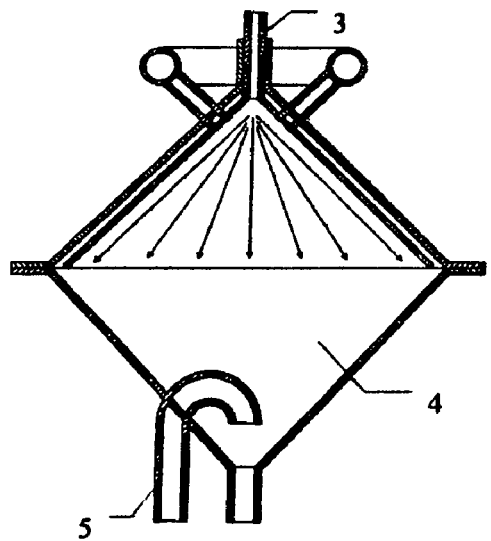

The device is illustrated in the attached drawings wherein FIG. 1 shows a schematic of the device and FIG. 2 shows the pressure and temperature conditioning chamber section.

In its preferred embodiment, device 100 contains (FIG. 1) a tank 1 including chamber 4 used to treat liquid product. Tank 1 is connected to pump 2 by a pipe to diffuser 3 (which is most preferably a stainless steel nozzle having an opening diameter of 1 to 3 mm). Nozzle 3 is in pressure and temperature conditioning chamber 4 that includes upper and lower parts that are connected to each other (and are preferably hermetically sealed) along the flanges. At the upper part of the chamber 4 there is nozzle 3, and the lower part of chamber 4 has vacuum control block 5, as best seen in FIG. 2. Device 100 further includes an optional heat source, which as shown is steam generator 6 connected via pressure control valve 7 to steam super heater 8, which in turn is connected to chamber 4 by a pipe. Device 100 also has cooling chamber 9 connected via pressure control valve 10 with condenser 11, tanks for condensation 12 and finished products 13, 14, and a vacuum pump 15 for creating a vacuum in chamber 4 in this embodiment.

In the most preferred aspect of a method according to the invention a liquid product is sent under pressure to diffuser (shown here as a nozzle) 3 where it is sprayed (or diffused) into chamber 4 from tank 1 via a pipe connected with nozzle 3. The diffusion is preferably performed at 20° C. temperature and the liquid product is preferably diffused into drops having a diameter generally not exceeding about 0.3 mm (although it is possible that some drops would exceed this diameter even in the preferred embodiment). The speed of pressure variation for the product is sufficient to kill a preselected microorganisms or microorganisms to a predetermined level, and this level is often required by a governmental standard. Determining the amount of pressure differential and (optionally) temperature required to kill a selected microbe in a selected liquid can be determined through trial and error. The pressure differential to which liquid is subjected can vary widely. For example, the pressure differential can vary between at least $10^5$ Pa/sec and no less than $10^9$ Pa/sec. In the preferred embodiment, the pressure differential to which the liquid product is subject is no less than $10^9$ Pa/sec. In another embodiment, the speed of pressure change in the liquid product is subject is at least $10^5$ Pa/sec.

Further, in this embodiment the pressure in the chamber is maintained at about 0.25 Pa, but it could be higher or lower since pressure differential per time is what kills the microorganisms. The pressure in chamber 4 is controlled by vacuum control block 5. The speed of the drops in chamber 4 is preferably about 10 m/sec or more, although this may vary according to desired operating parameters.

If heated, the liquid product is most preferably heated using steam from steam generator 6, which is regulated by valve 7. In this embodiment, steam is sent to steam super heater 8, where it is heated until it turns into a dry super heated water steam. Adding a steam super heater to the device is necessary for creating dry super heated water steam at low pressure before it enters chamber 4. The addition of vacuum control block 5 to chamber 4 is desired for steam regulation to maintain the pressure at the necessary level.

Steam from steam super heater 8 is then sent via a pipe connected to chamber 4 for direct mixing with the diffused liquid product. The steam is preferably injected into chamber 4 through a separate nozzle and is injected into the stream of diffused liquid product in the same direction as the diffused liquid product is moving. In this embodiment, the liquid product is heated at a speed not exceeding 1100° C./sec, although any suitable heating rate can be utilized. The product is heated to a temperature that does not lead to its qualitative changes, such temperatures being specific to each liquid product and being known to those skilled in the art. There is a balance between the stream condensation on drops of product and water evaporation from drops of product under achieved under certain conditions and parameters in the pressure and temperature treatment chamber. Optionally, the liquid product, if heated, could be heated using any other suitable method, such as infrared light or ultrasonic frequency, or by heating the walls of the chamber.

The treated product together with steam are sent to cooling chamber 9 where steam is removed with the help of condenser 11 and vacuum pump 15 and the product is cooled down to the required temperature which depends on valve opening 10. Removed steam in the form of condensate is sent to tank 12, while cooled product is sent to tank 13 or 14.

The use of the invention provides for microbiological stability of the treated liquid product while preserving qualitative properties of the liquid product at their original levels or close to them. This is an important feature for the industrial production of liquid products such as milk, juices (such as reconstituted juices or NFC juices), nectars and other products.

EXAMPLE 1

Fresh milk at 20° C. was sent under a pressure of 7 bar to chamber 4 from tank 1 via a pipe connected to diffuser 3. Diffuser 3 was of a type that diffused the milk into droplets having a diameter not exceeding about 0.3 mm, and in this example was a stainless steel nozzle. The speed of pressure reduction for the milk being diffused was $2.5\times10^9$ Pa/sec. The pressure at the diffuser was $6\times10^5$ Pa, the diameter of the outlet in the diffuser nozzle is 2 mm and the pressure in chamber 4 was held at 0.25 Pa, although other operating conditions may be utilized. The droplet speed of the diffused liquid product in chamber 4 was not less than 10 m/sec. Steam from steam generator 6 regulated by valve 7 was sent to steam super heater 8. Dry super-heated steam from steam super heater 8 was sent to chamber 4 for direct interaction with diffused fresh milk. The time during which the droplets of milk interacted with the steam was about 50 milliseconds. As a result the milk was heated to 65° C. which did not make any qualitative changes in it. The milk was heated from 20° C. to 65° C. at a heating rate of 900° C./sec. Treated milk and steam were then sent to cooling chamber 9 where, with the help of condenser 11 and vacuum pump 15, steam was removed and milk was cooled down to the target temperature of 31° C. which was controlled by valve opening 10, which was used to regulate water vaporation. Removed steam in the form of condensate was kept in tank 12, while the cooled milk was sent to tank 13.

The results of microbiological analysis of milk samples before and after pressure and temperature treatment proving the efficiency of the applied method and device are presented in Table 1, below:

TABLE 1

Results of the Microbiological Analysis of Treated Fresh Milk

| Microorganisms groups | CFU in 1 ml of milk | |
|---|---|---|
| | Before pressure and temperature treatment | After |
| Bacteria of the group of intestinal bacillus | 6 | 0 |
| General bacteria | $2.13 \times 10^2$ | 0 |
| Mezophile aerobic facultative anaerobic microorganisms | $1.7 \times 10^4$ | $3.2 \times 10^3$ |

EXAMPLE 2

The method was performed as described in Example 1, however NFC orange juice was used as the liquid product.

Table 2 illustrates the efficiency of the present method and device for NFC orange juice.

TABLE 2

Results of the Microbiological Analysis of NFC Orange Juice

| Microorganisms groups | CFU in 1 ml of NFC orange juice | |
|---|---|---|
| | Before pressure and temperature treatment | After |
| Mezophile aerobic facultative anaerobic microorganisms | $4.6 \times 10$ | 0 |
| Yeast | $5 \times 10$ | 0 |
| Mold | 4 | 0 |

EXAMPLE 3

The method was performed as described in Example 1, however physiological solution with *E. coli* culture was used as a liquid product.

Table 3 illustrates the efficiency of the present method and device for physiological solution with *E. coli* culture.

TABLE 3

Results of the Microbiological Analysis of Physiological Solution with *E. Coli* Culture

| Microorganisms groups | CFU in 1 ml of physiological solution | |
|---|---|---|
| | Before pressure and temperature treatment | After |
| *E. coli* | $3.9 \times 10^7$ | 0 |

Examples 1, 2, and 3 do not cover all applications for the invention and are illustrative only. For example the present method and device may also be used for pressure and optional temperature treatment of such liquid products as wine, foods, pharmaceuticals, blood plasma and others.

Having now described the invention, variations that do not depart from the scope of the invention will become available to those skilled in the art. The invention is thus not limited to the foregoing description but is set forth in the following claims and legal equivalents thereof. Unless explicitly stated otherwise, method steps according to the invention can be preformed in any order suitable of yielding a desired product.

What is claimed is:

1. A liquid product treatment method comprising:
   diffusing the liquid product into drops while passing the liquid product through a nozzle;
   heating the liquid product wherein the liquid product is directly mixed with a heating medium as the liquid product is diffused; and
   wherein:
   the liquid product is maintained at a first pressure on one side of the nozzle and is exposed to a pressure change by passing the liquid product through the nozzle into a chamber being maintained at a second pressure; and
   a speed of pressure change of the liquid product passing through the nozzle is sufficient to reduce a level of preselected microorganisms to a predetermined level.

2. The method of claim 1, wherein the speed of pressure change in the liquid product is approximately $10^5$ Pa/sec or more.

3. The method of 1, wherein the minimum pressure variation speed is approximately $10^9$ Pa/sec or more.

4. The method of claim 1 wherein the liquid product is heated as it is diffused.

5. The method of claim 4 wherein the liquid product is heated by steam and the steam is delivered into the chamber in the same direction as the liquid product is being diffused.

6. A liquid product treatment method comprising:
   diffusing the liquid product into drops while passing the liquid product through a nozzle;
   heating the liquid product as the liquid product is diffused; and
   wherein:
   the liquid product is heated by at least one of infrared radiation and ultra high frequency vibration;
   the liquid product is maintained at a first pressure on one side of the nozzle and is exposed to a pressure change by passing the liquid product through the nozzle into a chamber being maintained at a second pressure; and
   a speed of pressure change of the liquid product passing through the nozzle is sufficient to reduce a level of preselected microorganisms to a predetermined level.

7. A liquid product treatment method comprising:
   diffusing the liquid product into drops while passing the liquid product through a nozzle;
   heating the liquid product to a temperature not exceeding a temperature level effecting qualitative changes in the liquid product after the liquid product exits the nozzle; and
   wherein:
   the heating step is performed at pressure at or lower than ambient pressure;
   the liquid product is maintained at a first pressure on one side of the nozzle and is exposed to a pressure change by passing the liquid product through the nozzle into a chamber being maintained at a second pressure; and
   a speed of pressure change of the liquid product passing through the nozzle is sufficient to reduce a level of preselected microorganisms to a predetermined level.

8. A liquid product treatment method comprising:
   diffusing the liquid product into drops while passing the liquid product through a nozzle;
   heating the walls of a chamber into which the liquid product is diffused and;

wherein:
the liquid product is maintained at a first pressure on one side of the nozzle and is exposed to a pressure change by passing the liquid product through the nozzle into a chamber being maintained at a second pressure; and
a speed of pressure change of the liquid product passing through the nozzle is sufficient to reduce a level of preselected microorganisms to a predetermined level.

9. The method of claim 8 wherein the step of heating the walls of a chamber into which the liquid product is diffused further includes heating the walls of the chamber into which the liquid product is diffused without the liquid product having direct contact with the walls of the chamber.

* * * * *